United States Patent [19]

Bruschi

[11] Patent Number: 4,808,602

[45] Date of Patent: Feb. 28, 1989

[54] DERIVATIVES BASED UPON PYRIDO-MENADIONE ADDUCTS AND USE THEREOF AS FEED PREMIXES

[75] Inventor: Enrico Bruschi, Genoa, Italy

[73] Assignee: Heterochemical Corporation, Valley Stream, N.Y.

[21] Appl. No.: 12,019

[22] Filed: Feb. 9, 1987

Related U.S. Application Data

[63] Continuation-in-part of Ser. No. 834,322, Feb. 27, 1986, abandoned.

[51] Int. Cl.[4] .................. C07D 211/72; C07D 211/84; A61K 31/44
[52] U.S. Cl. .................................... 514/347; 546/301; 546/294
[58] Field of Search ................. 546/301, 294; 514/347

[56] References Cited

U.S. PATENT DOCUMENTS

| 3,328,169 | 6/1967 | Nanninga | 546/301 |
|---|---|---|---|
| 3,778,435 | 12/1973 | Nooi | 546/301 |
| 3,919,426 | 11/1975 | Nooi | 546/301 |
| 4,310,669 | 1/1982 | Althuis et al. | 546/294 |
| 4,390,543 | 6/1983 | Malhotra et al. | 546/301 |

OTHER PUBLICATIONS

Merck Index, 10th Ed., pp. 831 and 1151, 1983.

Primary Examiner—John M. Ford
Assistant Examiner—Robert C. Whittenbaugh
Attorney, Agent, or Firm—Brooks Haidt Haffner & Delahunty

[57] ABSTRACT

Novel adducts of menadione with pyridine derivatives, said compounds having vitamin $B_6$ activity and vitamin K activity, and being useful in animal feed premix and animal feed compositions.

6 Claims, 2 Drawing Sheets

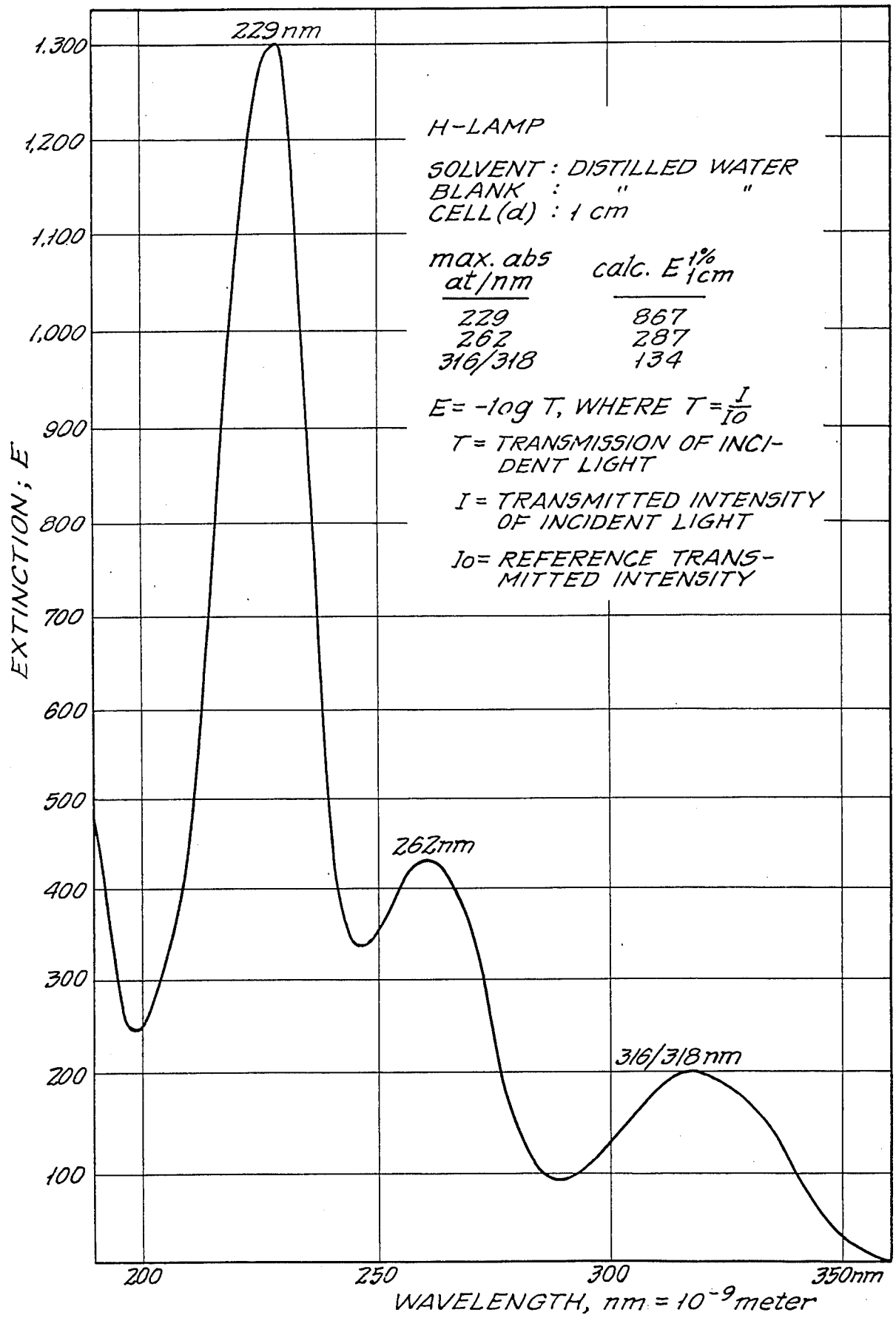

DERIVATIVES BASED UPON PYRIDO-MENADIONE ADDUCTS AND USE THEREOF AS FEED PREMIXES

CROSS REFERENCE TO RELATED APPLICATION

This application is a continuation-in-part of prior U.S. patent application Ser. No. 834,322, filed Feb. 27, 1986 now abandoned.

BACKGROUND OF THE INVENTION

1. Field of The Invention

The present invention relates to novel adducts of menadione with a derivative of pyridine such as pyridoxine, pyridoxal or pyridoxamine, which adduct has vitamin $B_6$ activity and vitamin K activity, and is useful in animal feed premix and compositions.

2. Description of The Prior Art

It has long been known that among the vitamin K active substances (VKAS) menadione sodium bisulfite (MSB), the adduct of of sodium bisulfite and menadione (2-methyl-1,4-naphthoquinone) provides better vitamin K (antihemorrhagic) activity on an equal weight basis than menadione itself. Menadione is one of the first synthetic analogues of the natural vitamin K's of vegetable or animal origin.

This quality has been partially explained on the basis of the high water solubility of the adduct (menadione is oil soluble) and the consequently easier and more effective absorption into the organism receiving this form of VKAS.

A further improvement was the discovery of the compound menadione dimethylpyrimidinol bisulfite (MPB) which is disclosed and described in U.S. Pat. No. 3,328,169 issued to Heterochemical Corporation, Valley Stream, N.Y. MPB is a compound in which the sodium atom of MSB was substituted by a weak organic base, more precisely a particular pyrimidine base. This resulting compound possessed a remarkably high vitamin K activity (P. Griminger, Poultry Science 44,210 (1965); Dua, Day ibid 45,94 (1966)) and a better stability than MSB when mixed with other vitamins, minerals, etc. in animal feed supplement.

SUMMARY OF THE INVENTION

This present invention relates to a family of novel adducts of menadione bisulfite with a compound exhibiting vitamin activity.

In particular, this family of compounds includes the three novel compounds having the formula I:

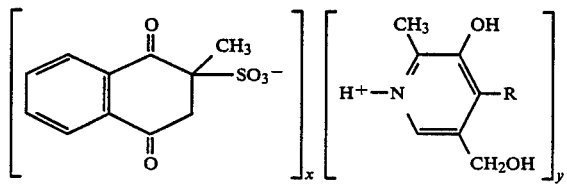

wherein x is two, y is one and R is —$CH_2N^+H_3$ or x is one, y is one and R is —$CH_2OH$ or —CHO.

This family of new compounds can be prepared by reacting a compound of the formula II:

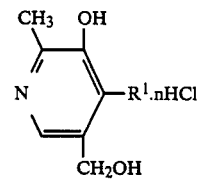

wherein
$R^1$ is —$CH_2OH$ and n=1, or
$R^1$ is —CHO and n=1, or
$R^1$ is —CHO and n=1, or
$R^1$ is —$CH_2NH_2$ and n=2,
with the selected molar amount of menadione sodium bisulfite.

The family of new compounds is useful as follows due to the combined vitamin K and $B_6$ activity.

The compounds of this invention may be utilized alone or in admixture with suitable carriers. They may be utilized with either acid or alkaline carriers because of their extreme stability. Numerous carriers are available and one is normally selected on the basis of cost, inertness to the compound and tolerance by the particular animal. The following list contains but a few of the nutritive materials which have been or may be employed as carriers: corn meal, corn cob meal, milo, soybean oil meal, alfalfa meal, dried whey, wheat shorts, distillers dried solubles, salt, meat scraps, calcite, feather meal, poultry by products, wheat middlings, dextrose, lactose meal, dried kelp, linseed oil meal, oatmeal, dried yeast, wheat bran, soybean meal and the like.

The compounds of this invention may be provided as premixes, or as concentrated mixtures, which may then be used to prepare the complete feed mixture. The premix is usually prepared to contain 4 grams of the compound per pound, however, multiple strength premixes, e.g. those containing 8, 12, 16, 24, 32 and 64 grams of the compound per pound can also be prepared and utilized. The premix can then be combined with other ingredients to form a complete feed, e.g. about one quarter pound of premix with about one ton of other ingredients will form a complete chicken feed. Complete feed for other animals can be similarily formulated. A complete feed composition can also be directly prepared containing from about 1 gram to about 20 grams of the desired compound per ton of composition without utilizing the premix composition.

The family of novel compounds according to the present invention has the following advantages.

The family of novel compounds is water soluble, but much less than MSB or menadione bisulfite complexes (MSBC). One of the advantages of the family of compounds according to the presently claimed invention is that they are moderately water soluble. A moderate water solubility is advantageous in certain uses. (See R. C. Wornick, Variation of Microingredients Assay Values on Feed Products; Causes and Solution; part II FEEDSTUFF, May 13, 1985, page 35). In regard to the vitamin K and $B_6$ activity, the compounds possess both activities.

Because VKAS and vitamin $B_6$ are generally added to poultry feed premixes and feed compositions in about equal amounts, the new compounds when used in such feeds, would allow for a saving of the quantity of vitamin $B_6$ to then be added. Another advantage over the prior art compounds, such as MSB, is a higher stability at high temperatures, high humidities and high pH's.

The first new compound is the 1,2,3,4-tetrahydro-2-methyl-1,4-dioxo-2-naphthalene sulfonic acid (menadione bisulfite) adduct with pyridoxamine in a molar ratio of 2:1. This compound possesses vitamin K activity (due to the menadione bisulfite moiety) as well as vitamin $B_6$ activity (due to the pyridoxamine moiety).

The first new compound of the present invention is 2-methyl-3-hydroxy-4-aminomethyl-5-hydroxymethyl-pyridine-bis(1,2,3,4-tetrahydro-2-methyl-1,4-dioxo-2-naphthalenesulfonate). It has the following empirical formula $C_{30}H_{32}N_2O_{12}S_2$. It has a melting point of 173°–175° C., is sparingly soluble in water at room temperature (1.3 g in 100 ml of water), and is poorly soluble in 99% ethyl alcohol, and in chloroform (less than 0.1 g in 100 ml). IR and UV spectra are shown in FIGS. 1 and 2, respectively.

It results from the substitution of the two atoms of sodium present in two molecules of MSB, with a weak, bi-functional organic base, namely 2-methyl-3-hydroxy-4-aminomethyl-5-hydroxymethylpyridine, having vitamin $B_6$ activity.

This first compound can be prepared by reacting MSB with pyridoxamine dihydrochloride in aqueous solution, in a molar ratio of 2:1, according to the following reaction scheme:

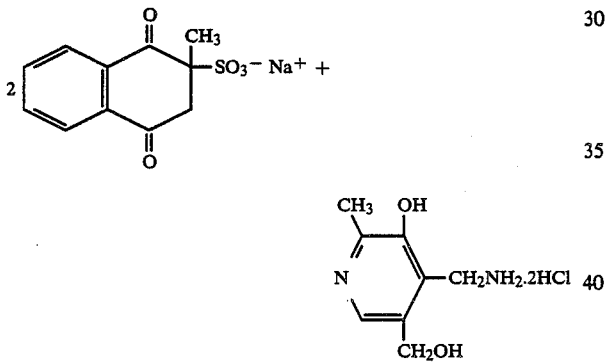

with elimination of two molecules of sodium chloride and precipitation of the compound in the form of white crystals.

Utility for the first new compound is based upon the fact that it contains, on a weight basis, almost the same amount of combined menadione compared to MSB, and 1.54 times more than MSBC. It contains 50.8% menadione and 24.8% vitamin $B_6$.

The second new compound is the menadione bisulfite adduct with pyridoxal in a molar ratio of 1:1. This compound posesses vitamin K activity (due to the menadione bisulfite moiety) as well as vitamin $B_6$ activity (due to the pyridoxal moiety).

The second new compound of the present invention is 2-methyl-3-hydroxy-4-formyl-5-hydroxymethylpyridine-1,2,3,4-tetrahydro-2-methyl-1,4-dioxo-2-naphthalenesulfonate having the empirical formula $C_{19}H_{19}O_8SN$. It results from the substitution of the one atom of sodium present in one molecule of MSB, with a weak, organic base, naamely 2-methyl-3-hydroxy-4-formyl-5-hydroxymethylpyridine, having vitamin $B_6$ activity.

This second compound can be prepared by reacting MSB with pyridoxal hydrochloride in aqueous solution, in a molar ratio of 1:1, according to the following reaction scheme:

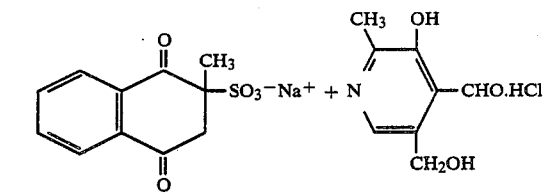

with elimination of one molecule of sodium chloride and precipitation of the compound in the form of a white material.

Utility for the second new compound is based upon the fact that it contains, on a weight basis, 40.9% menadione and 39.8% vitamin $B_6$.

The third new compound is the menadione bisulfite adduct with pyridoxine in a molar ratio of 1:1. This compound possesses vitamin K activity (due to the menadione bisulfite moiety) as well as vitamin $B_6$ activity (due to the pyridoxine moiety).

The third new compound of the invention is 2-methyl-3-hydroxy-4,5-dihydroxymethylpyridine-1,2,3,4-tetrahydro-2-methyl-1,4-dioxo-2-naphthalenesulfonate having the empirical formula $C_{19}H_{21}NO_8S$.

It results from the substitution of the one atom of sodium present in one molecule of MSB, with a weak, organic base, namely 2-methyl-3-hydroxy-4,5-dihydroxymethylpyridine, having vitamin $B_6$ activity.

This third compound can be prepared by reacting MSB with pyridoxine hydrochloride in aqueous solution, in a molar ratio of 1:1, according to the following reaction scheme:

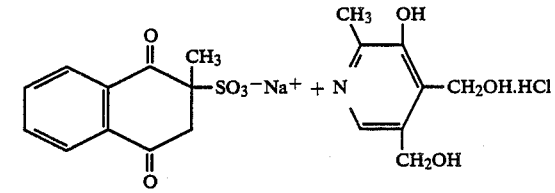

with elimination of one molecule of sodium chloride and precipitation of the compound in the form of a light yellow material.

A utility for the third new compound is based upon the fact that it contains, on a weight basis, 40.7% menadione and 40.06% vitamin $B_6$.

These and other advantages of the invention will be more fully understood from the following detailed description of the preferred embodiments of the invention, especially when that description is read in conjunction with the accompanying drawings. The drawings are not to be deemed limitative of the present invention in any manner thereof.

BRIEF DESCRIPTION OF THE DRAWINGS

FIG. 2 shows an ultraviolet spectrum for the compound, 2-methyl-3-hydroxy-4-aminomethyl-5-hydroxymethylpyridine-bis(1,2,3,4-tetrahydro-2-methyl-1,4-dioxo-2-naphthalenesulfonate).

DETAILED DESCRIPTION OF THE PREFERRED EMBODIMENTS

Figure 1:
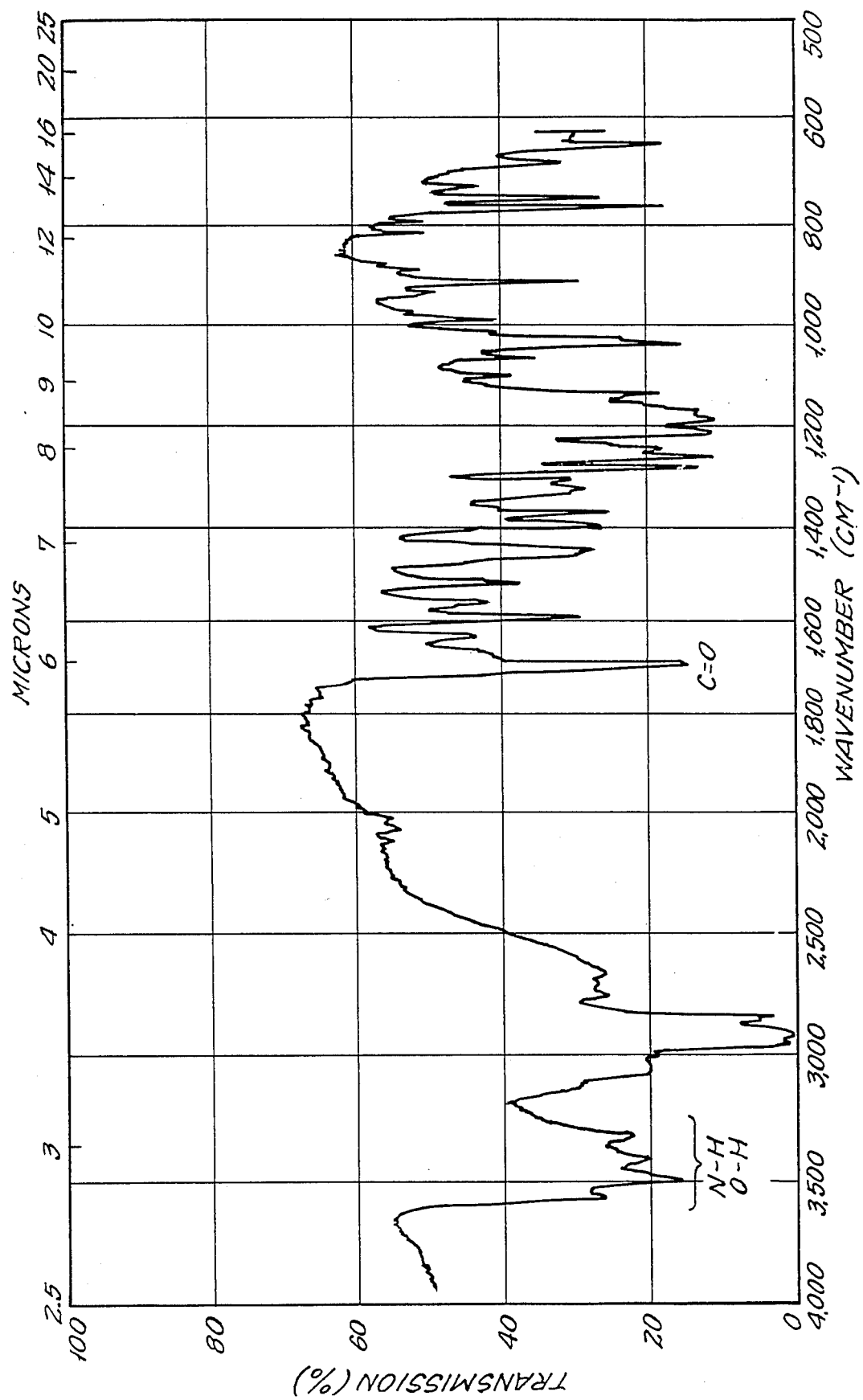
FIG. 1 shows an infrared spectrum for the compound 2-methyl-3-hydroxy-4-aminomethyl-5-hydroxymethyl-pyridine-bis(1,2,3,4-tetrahydro-2-methyl-1,4-dioxo-2-naphthalenesulfonate).

The preferred embodiments are illustrated by the following specific examples, which however, are not to be considered a limitation upon the present invention.

EXAMPLE 1

Preparation of Adduct of Menadione Bisulfite with Pyridoxamine

A solution containing 2.0 grams of pyridoxamine dihydrochloride, purity 98%, (0.00813 moles), in 10 ml of water, at room temperature, was added dropwise during 5 minutes, to a stirred solution of 5.2 grams of menadione sodium bisulfite, purity 95%, (0.01496 moles), in 13 ml of water. After a few minutes of stirring at a temperature of 25° C., a white crystalline precipitate formed. The product was filtered, washed with a few milliliters of ice cold water, then dried in vacuum at 40°-45° C. until constant weight was achieved. The recovered dry product was a white crystalline powder weighing 5.05 grams. The assay gave a combined menadione content equal to 48.5%, with a yield (based on MSB) equal to 95% and a purity of 95.3%. The so obtained compound melted, with decomposition, at 171°-173° C. The product was moderately soluble in water (1.3 g/100 ml of water).

EXAMPLE 2

Recrystallization 0.5 grams of the product prepared in Example 1 were dissolved in 15 ml of distilled water at 40°-50° C., and filtered through filter paper. The solution was chilled, while stirring, and the resulting crystals obtained were filtered and washed with a few milliliters of 96% ethanol, then dried in vacuum at 40° C.

The dry, white crystalline powder obtained was analyzed and had a combined menadione content of 50.8%; the pyridoxamine content was 24.8% (expressed as free base).

The elemental analysis gave the following results in percent by weight:

| Actual | Theoretical |
|---|---|
| C = 53.13% | C = 53.24% |
| H = 4.78% | H = 4.77% |
| N = 4.12% | N = 4.14% |
| O = 28.31% | O = 28.37% |
| S = 9.44% | S = 9.44% |

The recrystallized product corresponded to the empirical formula $C_{30}H_{32}N_2O_{12}S_2$. It had a melting point of 173°-175° C., was sparingly soluble in water at room temperature (1.3 g in 100 ml of water) and was poorly soluble in 99% ethyl alcohol and in chloroform (less than 0.1 g in 100 ml). IR and UV spectra are shown in FIGS. 1 and 2, respectively.

The first new compound was 2-methyl-3-hydroxy-4-aminomethyl-5-hydroxymethylpyridine-bis(1,2,3,4-tetrahydro-2-methyl-1,4-dioxo-2-naphthalenesulfonate). It had the empirical formula $C_{30}H_{32}N_2O_{12}S_2$ and had the molecular weight of 676.69. Its structural formula was:

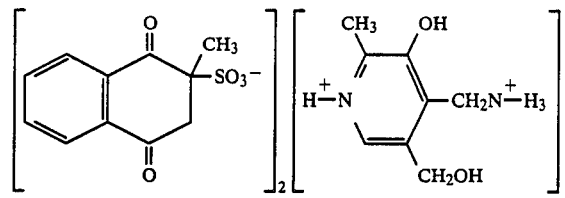

The first new compound is water soluble, but much less so than MSB or MSBC (1.3 g in 100 ml $H_2O$ versus 40-50 g in 100 ml). Water solubility is necessary for an easier and more effective absorption, but a too high water solubility for a microingredient, which is dosed in a final feed at levels of few ppm and which shows some degree of unstability, will cause faster loss in potency. A moderate water solubility is an advantage.

The vitamin activity, K and $B_6$, has been discussed above, and the new compounds of the invention when used in poultry feed, allow a saving in the quantity of vitamin $B_6$ to then be added thereto.

EXAMPLE 3

Preparation of Adduct of Menadione Bisulfite with Pyridoxal 3.0 grams of menadione sodium bisulfite, purity 95%, (0.00862 moles), were dissolved in 10 ml of water and the resulting solution filtered.

1.85 grams of pyridoxal hydrochloride, purity 98% (0.00866 moles), were dissolved in 10 ml of water and the resulting solution filtered.

The two solutions were combined and brought to dryness in a rotary evaporator. The residue was extracted with three 30 ml portions of a hot (40°-50° C.) ethanol/acetone (50/50) solution. The extracts were combined and brought to dryness in the rotary evaporator, and the residue was dried in vacuum at 40° C.

3.0 grams of a white amorphous mass, were obtained (yield 81%). The dry material obtained was pulverized and assayed for combined menadione content. Found 40.89%, theoretical 40.95%.

The second new compound was 2-methyl-3-hydroxy-4-formyl-5-hydroxymethylpyridine-1,2,3,4-tetrahydro-2-methyl-1,4-dioxo-2-naphthalenesulfonate, having the empirical formula $C_{19}H_{19}O_8SN$, containing 40.95% combined menadione ($C_{11}H_8O_2$) and 39.8% of pyridoxal. It had the following structural formula:

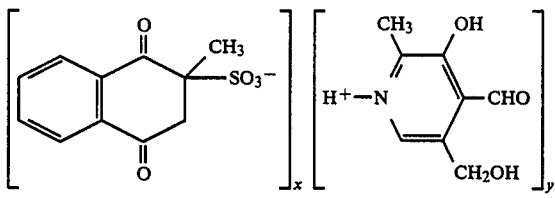

EXAMPLE 4

Preparation of Adduct of Menadione Bisulfite with Pyridoxine 3.0 grams of menadione sodium bisulfite, purity 95%, (0.00862 moles), were dissolved in 10 ml of water and the resulting solution filtered.

1.84 grams of pyridoxine hydrochloride, purity 99%, (0.00885 moles), were dissolved in 10 ml of water and the resulting solution filtered.

The two solutions were combined and brought to dryness in a rotary evaporator. The residue was extracted with three 30 ml portions of a hot ethanol/acetone (50/50) solution.

The extracts were combined and brought to dryness in the rotary evaporator, and the residue dried in vacuum at 40° C.

2.92 grams of a light yellow material were obtained (yield 78%). The dry material obtained was pulverized and assayed for combined menadione content. Found 40.68%, theoretical 40.77%.

The third new compound was 2-methyl-3-hydroxy-4,5-dihydroxymethylpyridine-1,2,3,4-tetrahydro-2-methyl-1,4-dioxo-2-naphthalenesulfonate, having the empirical formula $C_{19}H_{21}NO_8S$ containing 40.77% combined menadione ($C_{11}H_8O_2$) and 40.06% pyridoxine. It had the following structural formula:

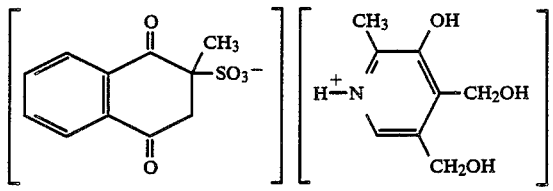

EXAMPLE 5

To compare VKAS stability, an accelerated test was conducted between menadione sodium bisulfite (Comparative) and the first new compound of the invention.

Each test was carried out by mixing the VKAS with calcium carbonate at a level of 0.5% of combined menadione. Then the mixture was steamed in a laboratory sterilizer at 7.5 psig for 2 to 4 minutes. After 4 minutes of steaming, the first new compund according to the invention showed a recovery of combined menadione equal to 40% of the original amount; whereas MSB gave only a 16% recovery. These stressed conditions are a simulation of the pelleting processes used to produce pellets containing a vitamin K substance. Based upon these tests, it can be seen that all three of the new compounds of the present invention would be more stable than MSB, during pelleting.

Thus the compounds of the invention have a higher stability at high temperatures, high humidities and high pH's than do the VKAS prior art compounds.

The above examples will illustrate in detail the manner in which the invention may be practiced. It will be understood, however, that the invention is not confined to the specific limitations set forth in the examples, but rather to the scope of the appended claims.

The embodiments of the invention in which an exclusive property or privilege is claimed are defined as follows:

1. A compound of the formula

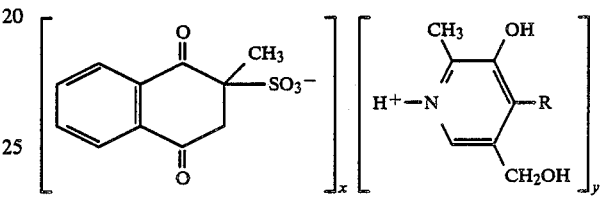

wherein x is two, y is one and R is $-CH_2N^+H_3$ or x is one, y is one and R is $-CH_2OH$ or $-CHO$.

2. A compound according to claim 1 wherein x is two, y is one, and R is $-CH_2N^+-H_3$.

3. A compound according to claim 1 wherein x is one, y is one, and R is $-CH_2OH$.

4. A compound according to claim 1 wherein x is one, y is one, and R is $-CHO$.

5. An animal feed premix containing a carrier and from about 4 to about 64 grams per pound of total premix of a compound according to claim 1.

6. An animal feed composition containing from about 1 gram per ton to about 20 grams per ton of total composition of a compound according to claim 1.

* * * * *